US008426379B2

(12) United States Patent
Yang et al.

(10) Patent No.: US 8,426,379 B2
(45) Date of Patent: Apr. 23, 2013

(54) POT1 ALTERNATIVE SPLICING VARIANTS

(75) Inventors: Qin Yang, St. Louis, MO (US); Curtis C. Harris, Garrett Park, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 13/027,854

(22) Filed: Feb. 15, 2011

(65) Prior Publication Data

US 2012/0016003 A1 Jan. 19, 2012

Related U.S. Application Data

(62) Division of application No. 11/665,944, filed as application No. PCT/US2005/037957 on Oct. 19, 2005, now Pat. No. 7,892, 738.

(60) Provisional application No. 60/620,754, filed on Oct. 20, 2004.

(51) Int. Cl.

| | |
|---|---|
| *C12N 15/11* | (2006.01) |
| *A61K 48/00* | (2006.01) |
| *C07H 21/02* | (2006.01) |
| *C07H 21/04* | (2006.01) |

(52) U.S. Cl.

USPC .......................................... 514/44 A; 536/24.5

(58) Field of Classification Search .................... 514/44; 536/24.5

See application file for complete search history.

(56) References Cited

U.S. PATENT DOCUMENTS 6,753,411 B2 6/2004 Baumann et al.

OTHER PUBLICATIONS

Kondo et al. Cancer Research, Jan. 15, 2004 vol. 64:523-529.*
Baumann et al., (Molecular and Cellular Biology), 22(22), pp. 8079-8087 (Nov. 2002).
Tockman et al., (Cancer Res.), vol. 52, pp. 2711s-2718s (1992).
Alberts et al., (Molecular Biology of the Cell—3rd Edition), p. 465 (1994).
Greenbaum et al., (Genome Biology), 4(9), pp. 117.1-117.8 (2003).
Yang et al., "Functional Diversity of Human Protection of Telomeres 1 Isoforms in Telomere Protection and Cellular Senescence" Cancer Res. 67:11677-11686 (2007).

* cited by examiner

*Primary Examiner* — Terra Cotta Gibbs

(74) *Attorney, Agent, or Firm* — Edwards Wildman Palmer LLP; Peter F. Corless

(57) ABSTRACT

The present invention provides methods and compositions for diagnosis and treatment of carcinomas with aberrant expression patterns of POT 1. The invention also provides methods of identifying compounds that may modulate the cellular expression of POT 1. The invention further provides methods for treating subjects suffering from or at risk of developing a colorectal carcinoma.

4 Claims, 6 Drawing Sheets

293 041 RKO BS8500 BS3509 MCF7 Calu Hela HT1080 Saos-2 SK-LU-1 HCT116 HCT15 HEC59

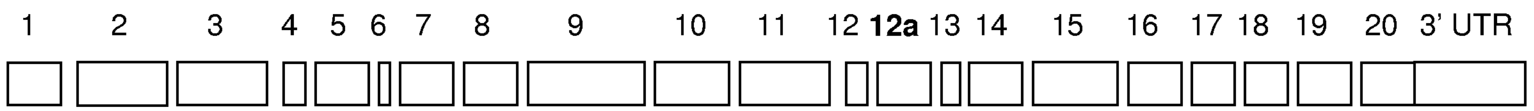

Figure 3

ATGGAGTCTCGCTTCGTCCTCCAGGCTGGAGTTCAGTGGCACGGTCTCGGCT
CATTGCAGCCTCCACCTCCTGAGTTCAAGCTTCTCCTGCCTCAGCCTCCCAAG
TAGCTGGGATTACAG (SEQ ID NO: 1)

Figure 4 mslvpatnyiytplnqlkggtivnvygvvkffkppylskgtdycsvvtivdqtnvkltcllfsgnyealpiiykngdivr
fhrlkiqvykketqgitssgfasltfegtlgapiiprtsskyfnfttedhkmvealrvwasthmspswtllklcdvqpmq
yfdltcqllgkaevdgasfllkvwdgtrtpfpswrvliqdlvlegdlshihrlqnltidilvydnhvhvarslkvgsflr
iyslhtklqsmnsenqtmlslefhlhggtsygrgirvlpesnsdvdqlkkdlesanltanqhsdvicqsepddsfpNG
VSLRPPGWSSVARSRLIAASTS* (SEQ ID NO: 2)

Figure 5

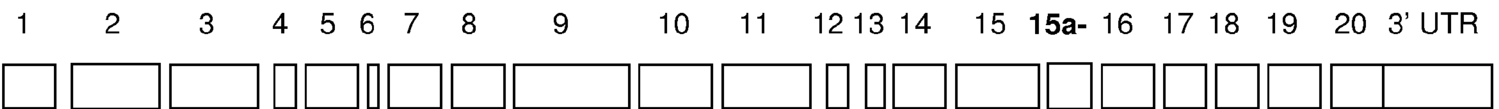

Figure 6

TTCTTCTGTAAGCTGGATATATCCCCTTTGTAAACAGAAGAGGAAACTGA
GACCAAGAGAAAATGGTGAAGTACTCAAG (SEQ ID NO: 3)

Figure 7

TTCTTCTGTAAGCTGGATATATCCCCTTTGTAAACAGAAGAGGAAACTGA
GACCAAGAGAAAATGGTGAAGTACTCAAGgttaaagacttaataaat* (SEQ ID NO: 4)

Figure 8 mslvpatnyiytplnqlkggtivnvygvvkffkppylskgtdycsvvtivdqtnvkltcllfsgnyealpiiykngdivr
fhrlkiqvykketqgitssgfasltfegtlgapiiprtsskyfnfttedhkmvealrvwasthmspswtllklcdvqpmq
yfdltcqllgkaevdgasfllkvwdgtrtpfpswrvliqdlvlegdlshihrlqnltidilvydnhvhvarslkvgsflr
iyslhtklqsmnsenqtmlslefhlhggtsygrgirvlpesnsdvdqlkkdlesanltanqhsdvicqsepddsfpssgs
vslyevercqqlsatiltdhqylertplcailkqkapqqyriraklrsykprrlfqsvklhcpkchllqevphegdldii
fqdgatktpvvklqntslydskiwttknqkgrkvavhfvknngilplsnecllllieVLL* (SEQ ID NO: 5)

Figure 9

15a agTTCTTCTGTAAGCTGGATATATCCCCTTTGTAAACAGAAGAGGAAACT

GAGACCAAGAGAAAATGGTGAAGTACTCAAGGTTAAAGACTTAATAAATgt (SEQ ID NO: 6)

15a- agTTCTTCTGTAAGCTGGATATATCCCCTTTGTAAACAGAAGAGGAAACT

GAGACCAAGAGAAAATGGTGAAGTACTCAAG (SEQ ID NO: 7)

SEQUENCE LISTING

```
<160> NUMBER OF SEQ ID NOS: 20

<210> SEQ ID NO 1
<211> LENGTH: 120
<212> TYPE: DNA
<213> ORGANISM: Homo sapiens

<400> SEQUENCE: 1

atggagtctc gcttcgtcct ccaggctgga gttcagtggc acggtctcgg ctcattgcag     60

cctccacctc ctgagttcaa gcttctcctg cctcagcctc ccaagtagct gggattacag    120


<210> SEQ ID NO 2
<211> LENGTH: 340
<212> TYPE: PRT
<213> ORGANISM: Homo sapiens

<400> SEQUENCE: 2

Met Ser Leu Val Pro Ala Thr Asn Tyr Ile Tyr Thr Pro Leu Asn Gln
  1               5                  10                  15

Leu Lys Gly Gly Thr Ile Val Asn Val Tyr Gly Val Val Lys Phe Phe
             20                  25                  30

Lys Pro Pro Tyr Leu Ser Lys Gly Thr Asp Tyr Cys Ser Val Val Thr
        35                  40                  45

Ile Val Asp Gln Thr Asn Val Lys Leu Thr Cys Leu Leu Phe Ser Gly
     50                  55                  60

Asn Tyr Glu Ala Leu Pro Ile Ile Tyr Lys Asn Gly Asp Ile Val Arg
 65                  70                  75                  80

Phe His Arg Leu Lys Ile Gln Val Tyr Lys Lys Glu Thr Gln Gly Ile
                 85                  90                  95
```

```
Thr Ser Ser Gly Phe Ala Ser Leu Thr Phe Glu Gly Thr Leu Gly Ala
            100                 105                 110

Pro Ile Ile Pro Arg Thr Ser Ser Lys Tyr Phe Asn Phe Thr Thr Glu
        115                 120                 125

Asp His Lys Met Val Glu Ala Leu Arg Val Trp Ala Ser Thr His Met
    130                 135                 140

Ser Pro Ser Trp Thr Leu Leu Lys Leu Cys Asp Val Gln Pro Met Gln
145                 150                 155                 160

Tyr Phe Asp Leu Thr Cys Gln Leu Leu Gly Lys Ala Glu Val Asp Gly
                165                 170                 175

Ala Ser Phe Leu Leu Lys Val Trp Asp Gly Thr Arg Thr Pro Phe Pro
            180                 185                 190

Ser Trp Arg Val Leu Ile Gln Asp Leu Val Leu Glu Gly Asp Leu Ser
        195                 200                 205

His Ile His Arg Leu Gln Asn Leu Thr Ile Asp Ile Leu Val Tyr Asp
    210                 215                 220

Asn His Val His Val Ala Arg Ser Leu Lys Val Gly Ser Phe Leu Arg
225                 230                 235                 240

Ile Tyr Ser Leu His Thr Lys Leu Gln Ser Met Asn Ser Glu Asn Gln
                245                 250                 255

Thr Met Leu Ser Leu Glu Phe His Leu His Gly Gly Thr Ser Tyr Gly
            260                 265                 270

Arg Gly Ile Arg Val Leu Pro Glu Ser Asn Ser Asp Val Asp Gln Leu
        275                 280                 285

Lys Lys Asp Leu Glu Ser Ala Asn Leu Thr Ala Asn Gln His Ser Asp
    290                 295                 300

Val Ile Cys Gln Ser Glu Pro Asp Asp Ser Phe Pro Asn Gly Val Ser
305                 310                 315                 320

Leu Arg Pro Pro Gly Trp Ser Ser Val Ala Arg Ser Arg Leu Ile Ala
                325                 330                 335

Ala Ser Thr Ser
            340


<210> SEQ ID NO 3
<211> LENGTH: 79
<212> TYPE: DNA
<213> ORGANISM: Homo sapiens

<400> SEQUENCE: 3

ttcttctgta agctggatat atccccttg taaacagaag aggaaactga gaccaagaga     60

aaatggtgaa gtactcaag                                                 79


<210> SEQ ID NO 4
<211> LENGTH: 97
<212> TYPE: DNA
<213> ORGANISM: Homo sapiens

<400> SEQUENCE: 4

ttcttctgta agctggatat atccccttg taaacagaag aggaaactga gaccaagaga     60

aaatggtgaa gtactcaagg ttaaagactt aataaat                             97


<210> SEQ ID NO 5
<211> LENGTH: 459
<212> TYPE: PRT
<213> ORGANISM: Homo sapiens

<400> SEQUENCE: 5
```

```
Met Ser Leu Val Pro Ala Thr Asn Tyr Ile Tyr Thr Pro Leu Asn Gln
1               5                   10                  15

Leu Lys Gly Gly Thr Ile Val Asn Val Tyr Gly Val Val Lys Phe Phe
            20                  25                  30

Lys Pro Pro Tyr Leu Ser Lys Gly Thr Asp Tyr Cys Ser Val Val Thr
        35                  40                  45

Ile Val Asp Gln Thr Asn Val Lys Leu Thr Cys Leu Leu Phe Ser Gly
    50                  55                  60

Asn Tyr Glu Ala Leu Pro Ile Ile Tyr Lys Asn Gly Asp Ile Val Arg
65                  70                  75                  80

Phe His Arg Leu Lys Ile Gln Val Tyr Lys Lys Glu Thr Gln Gly Ile
                85                  90                  95

Thr Ser Ser Gly Phe Ala Ser Leu Thr Phe Glu Gly Thr Leu Gly Ala
            100                 105                 110

Pro Ile Ile Pro Arg Thr Ser Ser Lys Tyr Phe Asn Phe Thr Thr Glu
        115                 120                 125

Asp His Lys Met Val Glu Ala Leu Arg Val Trp Ala Ser Thr His Met
    130                 135                 140

Ser Pro Ser Trp Thr Leu Leu Lys Leu Cys Asp Val Gln Pro Met Gln
145                 150                 155                 160

Tyr Phe Asp Leu Thr Cys Gln Leu Leu Gly Lys Ala Glu Val Asp Gly
                165                 170                 175

Ala Ser Phe Leu Leu Lys Val Trp Asp Gly Thr Arg Thr Pro Phe Pro
            180                 185                 190

Ser Trp Arg Val Leu Ile Gln Asp Leu Val Leu Glu Gly Asp Leu Ser
        195                 200                 205

His Ile His Arg Leu Gln Asn Leu Thr Ile Asp Ile Leu Val Tyr Asp
    210                 215                 220

Asn His Val His Val Ala Arg Ser Leu Lys Val Gly Ser Phe Leu Arg
225                 230                 235                 240

Ile Tyr Ser Leu His Thr Lys Leu Gln Ser Met Asn Ser Glu Asn Gln
                245                 250                 255

Thr Met Leu Ser Leu Glu Phe His Leu His Gly Gly Thr Ser Tyr Gly
            260                 265                 270

Arg Gly Ile Arg Val Leu Pro Glu Ser Asn Ser Asp Val Asp Gln Leu
        275                 280                 285

Lys Lys Asp Leu Glu Ser Ala Asn Leu Thr Ala Asn Gln His Ser Asp
    290                 295                 300

Val Ile Cys Gln Ser Glu Pro Asp Asp Ser Phe Pro Ser Ser Gly Ser
305                 310                 315                 320

Val Ser Leu Tyr Glu Val Glu Arg Cys Gln Gln Leu Ser Ala Thr Ile
                325                 330                 335

Leu Thr Asp His Gln Tyr Leu Glu Arg Thr Pro Leu Cys Ala Ile Leu
            340                 345                 350

Lys Gln Lys Ala Pro Gln Gln Tyr Arg Ile Arg Ala Lys Leu Arg Ser
        355                 360                 365

Tyr Lys Pro Arg Arg Leu Phe Gln Ser Val Lys Leu His Cys Pro Lys
    370                 375                 380

Cys His Leu Leu Gln Glu Val Pro His Glu Gly Asp Leu Asp Ile Ile
385                 390                 395                 400

Phe Gln Asp Gly Ala Thr Lys Thr Pro Val Val Lys Leu Gln Asn Thr
                405                 410                 415

Ser Leu Tyr Asp Ser Lys Ile Trp Thr Thr Lys Asn Gln Lys Gly Arg
```

```
        420                 425                 430

Lys Val Ala Val His Phe Val Lys Asn Asn Gly Ile Leu Pro Leu Ser
        435                 440                 445

Asn Glu Cys Leu Leu Leu Ile Glu Val Leu Leu
    450                 455


<210> SEQ ID NO 6
<211> LENGTH: 101
<212> TYPE: DNA
<213> ORGANISM: Homo sapiens

<400> SEQUENCE: 6

agttcttctg taagctggat atatcccctt tgtaaacaga agaggaaact gagaccaaga     60

gaaaatggtg aagtactcaa ggttaaagac ttaataaatg t                        101


<210> SEQ ID NO 7
<211> LENGTH: 81
<212> TYPE: DNA
<213> ORGANISM: Homo sapiens

<400> SEQUENCE: 7

agttcttctg taagctggat atatcccctt tgtaaacaga agaggaaact gagaccaaga     60

gaaaatggtg aagtactcaa g                                               81


<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

ttcagatgtt atctgtcaat cagaacctg                                       29


<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

ggaggtggag gctgcaatga g                                               21


<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

atgtctactt ttgatagaag                                                 20


<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 11
tgagtgtacc tccttgagta 20

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
atgtattgtt ccttgtataa gaaatggtgc 30

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tagccttcat accaaacttc aatc 24

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ttatatccaa atcgccctca t 21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gggcaaagca gaagtggacg gagcatc 27

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
acgaggtaga aagatgtcaa 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

-continued tgagtgtacc tccttgagta 20

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Asn Gly Val Ser Leu Arg Pro Pro Gly Trp Ser Ser Val Ala Arg Ser
1 5 10 15

Arg Leu Ile Ala Ala Ser Thr Ser
20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
cctgagttca agcttctcc 19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
aagtactcaa ggaggtaca 19

POT1 ALTERNATIVE SPLICING VARIANTS

RELATED APPLICATIONS

This application is a Divisional of U.S. application Ser. No. 11/665,944, filed May 22, 2008, now U.S. Pat. No. 7,892,738, which is a 35 U.S.C. §371 U.S. national entry of International Application PCT/US2005/037957 (WO 2006/045062) having an International filing date of Oct. 19, 2005, which claims priority from U.S. Provisional Application No. 60/620,754, entitled "POT1 Alternative Splicing" filed Oct. 20, 2004, all of which applications are hereby incorporated by reference in their entirety.

STATEMENT REGARDING FEDERALLY SPONSORED RESEARCH OR DEVELOPMENT

Research supporting this application was carried out by the United States of America as represented by the Secretary, Department of Health and Human Services.

FIELD OF THE INVENTION

The present invention features methods of diagnosing colorectal carcinoma and screening assays for identifying modulators POT1 expression. Further provided are methods for treating subjects suffering from or at risk of developing colorectal carcinoma.

BACKGROUND OF THE INVENTION

Hereditary nonpolyposis colorectal carcinoma (HNPCC) is the most commonly occurring hereditary disorder that predisposes a person to colorectal carcinoma (CRC). It accounts for approximately 2-7% of all CRC cases diagnosed in the United States each year. Its diagnosis is difficult and wholly dependent on a meticulously obtained family history of cancer of all anatomic sites, with particular attention to the pattern of cancer distribution throughout the family. PCR technology is able to provide a fast, sensitive, and accurate diagnosis of other tumor types with microsatellite instability. The advantages of having a cost effective and fast diagnostic method for a previously difficult to diagnosis disease underscores the potential commercial viability of a method for the diagnosis, treatment and/or prevention of CRC using such methods.

There is an urgent need to diagnose and treat subjects with CRC, and to prevent tumors in subjects susceptible to such tumors. Presently, the ability to correctly diagnose CRC tumors types is limited and often leads to less effective treatments. Therefore, simple, accurate methods that diagnose, prevent, and/or treat susceptible subjects would have a significant impact in the ultimate eradication of such diseases.

BRIEF SUMMARY OF THE INVENTION

We now provide new methods and compositions for the diagnosis and treatment of carcinomas with aberrant expression patterns of POT1.

According to one aspect, an isolated POT1 12a protein splice variant is presented. In a related aspect, an isolated POT1 15a- protein splice variant is presented.

According to another aspect, a non-genomic polynucleotide of the POT1 12a splice variant is presented. In a related aspect, a non-genomic polynucleotide of the POT1 15a- splice variant is presented.

According to another aspect, an antibody that specifically recognizes the POT1 12a splice variant is presented.

In another aspect, a method of diagnosis of a digestive tract tumor is presented and comprises detecting the expression of a POT1 splice variant. In a related aspect, a method of assessing the risk of developing a digestive tract disorder by determining the POT1 splice variant expression is presented.

In another aspect, a method of treating a digestive tract disorder comprises, administering to a subject an effective amount of an RNA that inactivates the POT1 15a, POT1 15a-, and/or the POT1 12a splice variants.

Other embodiments of the invention are disclosed infra.

BRIEF DESCRIPTION OF THE DRAWINGS

FIG. 2 depicts the structure of the POT1 splice variant 12a. The exons are shown as white boxes.

FIG. 3 depicts the cDNA sequence Exon 12a of the POT1 splice variant 12a (SEQ ID NO: 1).

FIG. 4 depicts the protein sequence of POT1 splice variant 12a (SEQ ID NO: 2). The capital letters depict the unique sequences of the variant.

FIG. 5 depicts the structure of the POT1 splice variant 15-. The exons are shown as white boxes.

FIG. 6 depicts the Exon 15a- cDNA sequence of the POT1 splice variant 15a- (SEQ ID NO: 3).

FIG. 7 depicts the Exon 15a cDNA sequence (SEQ ID NO: 4). The lower case letters show the extra sequences compared with variant 15a-.

FIG. 8 depicts the protein sequence of the POT1 splice variant 15a- (SEQ ID NO: 5). The capital letters represent unique sequences of variant 15a.

FIG. 9 depicts the sequences of the exons 15a (SEQ ID NO: 6) and 15a- (SEQ ID NO: 7) of POT1.

FIG. 11A graphically depicts the results as % amplification of POT1 variant 12a amplified with 12a/12aB primers from MMR− and MMR+ cell lines. FIG. 11B graphically depicts the results as % amplification of POT1 variant 15a- amplified with primers 15A/15aB2 primers from MMR− and MMR+ cell lines.

DETAILED DESCRIPTION OF THE INVENTION

Figure 1:
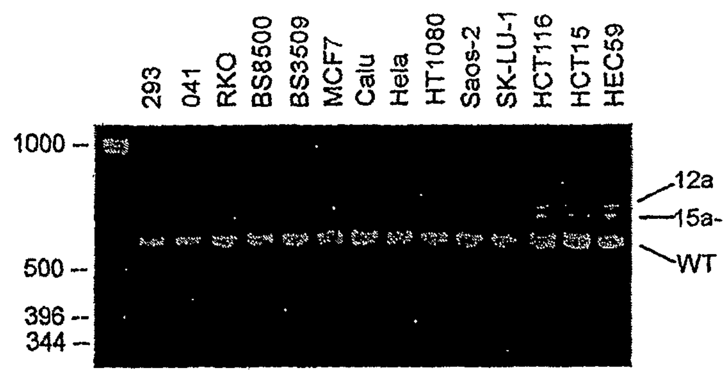
FIG. 1 depicts POT1 alternative splicing variants in human cell lines. Exons 12 to 16 of POT1 cDNA were amplified to detect the presence of different splice forms. The two additional bands, marked 12a and 15a-, representing the alternately spliced forms of POT112a and POT115- were found in mismatch repair deficient (RKO, HCT116, HCT15, and HEC59), but not proficient, human cell lines. The lower band is the wild-type POT1 cDNA. The medium band is 15a- cDNA, a novel variant of POT1, which lacks the last 18 base pairs of 15a (variant 5) that is only present in leukocytes. The upper band is 12a (variant 2).
Figure 10:
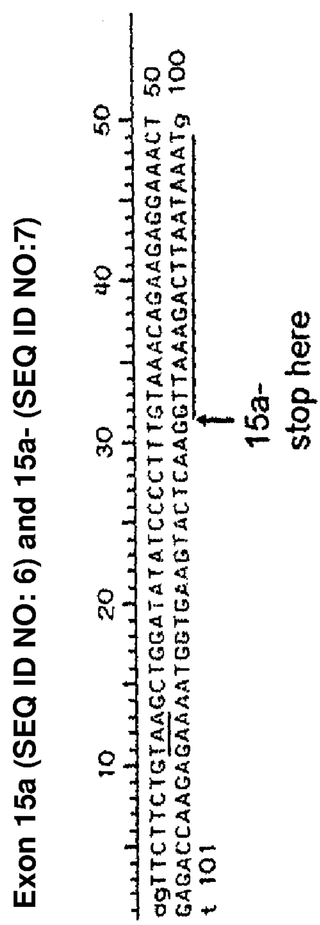
FIG. 10 depicts the sequence of the 15a (SEQ ID NO: 6) and the 15a- (SEQ ID NO: 7) exons of POT1.

We now provide new methods and compositions for diagnosis and treatment of carcinomas with aberrant expression patterns of POT1. The invention also provides methods of identifying compounds that may modulate the cellular expression of POT1. The invention further provides methods for treating subjects suffering from or at risk of developing a colorectal carcinoma. The methods surprisingly provide a precise, efficient, easy, and accurate method of diagnosing CRC, which has been unavailable and long sought after in the art.

Telomere proteins from ciliated protozoa bind to the single-stranded G-rich DNA extensions at the end of macronuclear chromosomes. Baumann and Cech, (Pott, the putative telomere end-binding protein in fission yeast and humans, Science, 2001, 292(5519):1171-5. Erratum in: Science 2001, 293(5528):214.), a human homologous was identified and called Pott for 'protection of telomeres.' POT1 binds telomeric repeat sequences. Studies have shown that the deletion of the fission yeast Pot1 gene has an effect on chromosome stability. Baumann and Cech (2001). A mutant form of POT1, which lacks the DNA-binding domain abrogated TRF1-mediated control of telomere length, and induces telomere elongation.

Baumann and Cech (2001) identified the human POT1 sequence by a database search with the *S. pombe* Pot1 protein sequence, and cloned the gene from ovary cDNA. POT1 encodes a one protein of 109 amino acids that is 26% identical to the *S. pombe* Pot1 protein. The 109 amino acid protein has been shown to be ubiquitously expressed, which is consistent with the idea that POT1 is a housekeeping gene. The 71-kD peptide binds to the G-rich strand of human telomeric DNA. In contrast, binding was not observed with the complementary C-rich strand or with double-stranded telomeric DNA.

Lei et al. (2003) described the 1.9-angstrom resolution crystal structure of the N-terminal DNA-binding domain of *S. pombe* Pot1 protein complexed with single-stranded DNA. (DNA self-recognition in the structure of Pot1 bound to telomeric single-stranded DNA, Nature, 2003, 426(6963):198-203.). The protein adopts an oligonucleotide/oligosaccharide-binding (OB) fold with 2 loops that protrude to form a clamp for single-stranded DNA binding. The structure explains the sequence specificity of binding: in the context of the Pot1 protein, DNA self-recognition involving base-stacking and unusual G-T basepairs compacts the DNA. Any sequence change disrupts the ability of the DNA to form this structure, preventing it from contacting the array of protein hydrogen-bonding groups. Lei et al. (2003) concluded that the structure also explains how Pot1 protein avoids binding the vast excess of RNA in the nucleus.

I. Screening Assays:

The invention provides methods (also referred to herein as "screening assays") for identifying modulators, i.e., candidate or test compounds or agents (e.g., peptides, peptidomimetics, small molecules, ribozyme, siRNA, RNAi, ribozyme, tRNA, mRNA, a ribosomal RNA, snRNA, 5SRNA, an active portion of an RNP, or a POT1 antisense molecule) which bind to POT1 proteins, have a stimulatory or inhibitory effect on POT1 expression or POT1 activity, or have an inhibitory effect on the expression or activity of a POT1 target molecule. Modulators identified using the assays described herein may be useful for treating a digestive tract tumor, for example, CRC.

Modulators include, for example, 1) peptides such as soluble peptides, including Ig-tailed fusion peptides and members of random peptide libraries (see, e.g., Lam, K. S. Et al. (1991) Nature 354:82-84; Houghten, R. Et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

The modulators of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

In one aspect, an assay is a cell-based assay in which a cell which expresses a POT1 protein or biologically active portion thereof is contacted with a test compound, and the ability of the test compound to modulate POT1 activity is determined. In a preferred embodiment, the biologically active portion of the POT1 protein is either the 15a- or the 12 a variant. Determining the ability of the test compound to modulate POT1 activity can be accomplished by monitoring, for example, the POT1mRNA expression in the cell (e.g., Northern blotting, quantitative PCR (e.g., RT-PCR), or in vitro transcriptional assays). The cell, for example, can be of mammalian origin, e.g., a mismatch repair deficient cell.

To perform an in vitro transcriptional assay, the full length promoter and enhancer of POT1 can be linked to a reporter gene such as chloramphenicol acetyltransferase (CAT), luciferase, or a fluorescent protein (e.g., GFP and variants thereof) and introduced into host cells. The same host cells can then be transfected with or contacted with the test compound. The effect of the test compound can be measured by reporter gene activity and comparing it to reporter gene activity in cells which do not contain the test compound. A decrease in reporter gene activity indicates a modulation of POT1 expression and is, therefore, an indicator of the ability of the test compound to modulate the expression of POT1.

II. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining POT1 protein and/or nucleic acid expression as well as POT1 activity, in the context of a biological sample (e.g., blood, serum, cells, or tissue, e.g., colon tissue, tumor cells or muscle tissue) to thereby determine whether an individual is afflicted with a digestive tract tumors, for example, CRC. The invention also provides for prognostic (or predictive) assays for determining whether an individual is at risk of developing digestive tract tumors, for example, CRC. For example, the expression of alternate forms of the POT1 gene, for example the 15a- or the 12a variant, can be assayed for in a biological sample. Such assays can be used for prognostic or predictive purpose to thereby prophylactically treat an individual prior to the onset of a digestive tract tumor, for example, CRC.

Another aspect of the invention pertains to monitoring the influence of POT1 modulators (e.g., anti-POT1 antibodies, ribozymes, or small molecules) on the expression or activity of POT1 in clinical trials.

These and other agents are described in further detail in the following sections.

A. Diagnostic Assays for Digestive Tract Tumors

To determine whether a subject is afflicted with a digestive tract tumor, for example, CRC, a biological sample may be obtained from a subject and the biological sample may be contacted with a compound or an agent capable of detecting a POT1 protein or nucleic acid (e.g., mRNA or genomic DNA of the POT1 12a or 15a- splice variants) that encodes a POT1 protein, in the biological sample. A preferred agent for detecting POT1 mRNA or genomic DNA is a labeled nucleic acid probe capable of hybridizing to POT1 mRNA or genomic DNA. The nucleic acid probe can be, for example, the POT1 nucleic acid set forth in FIGS. 3, 6, 7, and/or 9, or a portion thereof, such as an oligonucleotide of at least 15, 20, 25, 30, 25, 40, 45, 50, 100, 250 or 500 nucleotides in length and sufficient to specifically hybridize under stringent conditions to POT1 mRNA or genomic DNA. Other suitable probes for use in the diagnostic assays of the invention are described herein.

A preferred agent for detecting POT1 protein in a sample is an antibody capable of binding to POT1 protein, preferably an antibody with a detectable label. Preferably an antibody specific for either the 12a and/or the 15a- splice variants. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of direct substances that can be coupled to an antibody or a nucleic acid probe include various enzymes, prosthetic groups, fluorescent materials, luminescent materials, bioluminescent materials, and radioactive materials. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect POT1 mRNA, protein, or genomic DNA in a biological sample in vitro as well as in vivo. For example, in vitro techniques for detection of POT1 mRNA include Northern hybridizations and in situ hybridizations. In vitro techniques for detection of POT1 protein include enzyme linked immunosorbent assays (ELISAs), Western blots, immunoprecipitations and immunofluorescence. In vitro techniques for detection of POT1 genomic DNA include Southern hybridizations. Furthermore, in vivo techniques for detection of POT1 protein include introducing into a subject a labeled anti-POT1 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting POT1 protein, mRNA, or genomic DNA, such that the presence of POT1 protein, mRNA or genomic DNA is detected in the biological sample, and comparing the presence of POT1 protein, nRNA or genomic DNA in the control sample with the presence of POT1 protein, mRNA or genomic DNA in the test sample.

B. Prognostic Assays for Digestive Tract Tumors

The present invention further pertains to methods for identifying subjects having or at risk of developing a digestive tract tumor, for example, CRC with aberrant POT1 expression or activity.

As used herein, the term "aberrant" includes a POT1 expression or activity, which deviates from the wild type POT1 expression or activity. Aberrant expression or activity includes increased or decreased expression or activity, as well as expression or activity, which does not follow the wild type developmental pattern of expression or the subcellular pattern of expression. For example, aberrant POT1 expression or activity is intended to include the expression of the 15a- and/or the expression of the 12a variant, as well as cases in which a mutation in the POT1 gene causes the POT1 gene to be under-expressed or over-expressed and situations in which such mutations result in a non-functional POT1 protein or a protein which does not function in a wild-type fashion, e.g., a protein which does not interact with a POT1 substrate, or one which interacts with a non-POT1 substrate.

The assays described herein, such as the preceding diagnostic assays or the following assays, can be used to identify a subject having or at risk of developing a digestive tract tumor, for example, CRC. A biological sample may be obtained from a subject and tested for the presence or absence of a genetic alteration. For example, such genetic alterations can be detected by ascertaining the existence of at least one of 1) a deletion of one or more nucleotides from a POT1 gene, 2) an addition of one or more nucleotides to a POT1 gene, 3) a substitution of one or more nucleotides of a POT1 gene, 4) a chromosomal rearrangement of a POT1 gene, 5) an alteration in the level of a messenger RNA transcript of a POT1 gene, 6) aberrant modification of a POT1 gene, such as of the methylation pattern of the genomic DNA, 7) the presence of a non-wild type splicing pattern of a messenger RNA transcript of a POT1 gene, 8) a non-wild type level of a POT1-protein, 9) allelic loss of a POT1 gene, 10) inappropriate post-translational modification of a POT1-protein, and/or 11) expression of the 15a- and/or the 12a splice variants of POT1.

As described herein, there are a large number of assays known in the art which can be used for detecting genetic alterations in a POT1 gene. For example, a genetic alteration in a POT1 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a POT1 gene (see Abravaya et al. (1995) Nucleic Acids Res. 23:675-682). This method includes collecting a biological sample from a subject, isolating nucleic acid (e.g., genomic DNA, mRNA or both) from the sample, contacting the nucleic acid sample with one or more primers which specifically hybridize to a POT1 gene under conditions such that hybridization and amplification of the POT1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers. Exemplary PCR primers are shown in Example 4.

In an alternative embodiment, mutations in a POT1 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in POT1 can be identified by hybridizing biological sample derived and control nucleic acids, e.g., DNA or RNA, to high density arrays containing hundreds or thousands of oligonucleotide probes (Cronin, M. T. et al. (1996) Hum. Mutat. 7:244-255; Kozal, M. J. Et al (1996) Nat. Med. 2:753-759). For example, genetic mutations in POT1 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the POT1 gene in a biological sample and detect mutations by comparing the sequence of the POT1 in the biological sample with the corresponding wild-type (control) sequence. Examples of sequencing reactions include those based on techniques developed by Maxam and Gilbert (1977) Proc. Natl. Acad. Sci. USA 74:560) or Sanger (1977) Proc. Natl. Acad. Sci. USA 74:5463). It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the POT1 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type POT1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217: 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in POT1 cDNAs obtained from samples of cells.

According to an exemplary embodiment, a probe based on a POT1 sequence, e.g., a wild-type POT1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in POT1 genes. For example, single strand conformation polymorphism (SSCP) may be used to detect differences in electrophoretic mobility between mutant and wild type nucleic acids (Orita et al. (1989) Proc Natl. Acad. Sci. USA 86:2766; see also Cotton (1993) Mutat. Res. 285:125-144 and Hayashi (1992) Genet. Anal. Tech. Appl. 9:73-79). Single-stranded DNA fragments of sample and control POT1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313: 495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell. Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a POT1 modulator (e.g., an agonist, antagonist, peptidomimetic, protein, peptide, nucleic acid, or small molecule) to effectively treat a digestive tract tumor, for example, CRC.

C. Monitoring of Effects During Clinical Trials

The present invention further provides methods for determining the effectiveness of a POT1 modulator (e.g., a POT1 modulator identified herein) in treating a digestive tract tumor, for example, CRC in a subject. For example, the effectiveness of a POT1 modulator in decreasing certain variants of POT1 from being expressed, protein levels of the 12a and 15a- variants can be monitored in clinical trials of subjects exhibiting expression of the 12a and 15a- variants of POT1. Alternatively, the effectiveness of a POT1 modulator in decreasing expression of the 12a and 15a- variants of POT1 gene expression, protein levels, or in downregulating POT1 activity, can be monitored in clinical trials of subjects exhibiting increased POT1 gene expression, protein levels, or POT1 activity. In such clinical trials, the expression or activity of a POT1 gene, and optionally, other genes that have been implicated in, for example, a digestive tract tumor, for example, CRC can be used as a “read out” or marker of the phenotype of a particular cell.

To study the effect of agents which modulate POT1 activity on subjects suffering from CRC, for example, a clinical trial, cells can be isolated and RNA prepared and analyzed for the levels of expression of POT1 and other genes implicated in the a digestive tract tumor, for example, CRC. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of POT1 or other genes. In this way, the gene expression pattern can serve as a marker, indicative of the physiological response of the cells to the agent which modulates POT1 activity. This response state may be determined before, and at various points during treatment of the individual with the agent which modulates POT1 activity.

In a preferred embodiment, the present invention provides a method for monitoring the effectiveness of treatment of a subject with an agent which modulates POT1 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a POT1 protein, mRNA, or genomic DNA in the pre-administration sample; (iii) obtaining one or more post-administration samples from the subject; (iv) detecting the level of expression or activity of the POT1 protein, mRNA, or genomic DNA in the post-administration samples; (v) comparing the level of expression or activity of the POT1 protein, mRNA, or genomic DNA; and (vi) altering the administration of the agent to the subject accordingly. For example, increased administration of the agent may be desirable to increase the expression or activity of certain POT1 splice variants to higher levels than detected, i.e., to increase the effectiveness of the agent. Alternatively, decreased administration of the agent may be desirable to decrease expression or activity of certain POT1 splice variants to lower levels than detected. According to such an embodiment, POT1 expression or activity may be used as an indicator of the effectiveness of an agent, even in the absence of an observable phenotypic response.

III. Methods of Treatment of Subjects Suffering from Digestive Tract Tumors:

The present invention provides for both prophylactic and therapeutic methods of treating a subject, e.g., a human, at risk of (or susceptible to) a digestive tract tumor, for example, CRC. As used herein, “treatment” of a subject includes the application or administration of a therapeutic agent to a subject, or application or administration of a therapeutic agent to a cell or tissue from a subject, who has a diseases or disorders has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a “therapeutic agent” includes, but is not limited to, small molecules, peptides, polypeptides, antibodies, ribozymes, and antisense oligonucleotides.

A. Prophylactic Methods

In one aspect, the invention provides a method for preventing in a subject, CRC by administering to the subject an agent which modulates POT1 expression or POT1 activity. Subjects at risk for a digestive tract tumor, for example, CRC can be identified by, for example, any or a combination of the diagnostic or prognostic assays described herein. Administration of a prophylactic agent can occur prior to the manifestation of symptoms characteristic of aberrant POT1 expression or activity, such that a digestive tract tumor, for example, CRC is prevented or, alternatively, delayed in its progression. Depending on the type of POT1 aberrancy, for example, a POT1 molecule, POT1 agonist or POT1 antagonist agent can be used for treating the subject. The appropriate agent can be determined based on screening assays described herein.

B. Therapeutic Methods

Another aspect of the invention pertains to methods for treating a subject suffering from a digestive tract tumor, for example, CRC. These methods involve administering to a subject an agent, which modulates POT1 expression or activity (e.g., an agent identified by a screening assay described herein), or a combination of such agents. In another embodiment, the method involves administering to a subject a POT1 protein or nucleic acid molecule as therapy to compensate for reduced, aberrant, or unwanted POT1 expression or activity.

Stimulation of POT1 activity is desirable in situations in which POT1 is abnormally downregulated and/or in which increased POT1 activity is likely to have a beneficial effect. Likewise, inhibition of POT1 activity is desirable in situations in which splice variants POT1 are abnormally upregulated and/or in which decreased POT1 activity is likely to have a beneficial effect, thereby ameliorating a digestive tract tumor, for example, CRC associated with aberrant expression of POT1 splice variants, 12a and 15a-.

The agents which modulate POT1 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradeimal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates POT1 activity in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate POT1 activity can also be prepared in the form of suppositories (e.g., with conventional suppository bases such as cocoa butter and other glycerides) or retention enemas for rectal delivery.

In one embodiment, the agents that modulate POT1 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates POT1 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such POT1 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents that modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies for Immunotargeting of Drugs in Cancer Therapy," in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review," in Monoclonal Antibodies '84: Biological and Clinical Applications, Pinchera et al. (eds.), pp. 475-506 (1985); "Analysis, Results, and Future Prospective of the Therapeutic Use of Radiolabeled Antibody in Cancer Therapy", in Monoclonal Antibodies for Cancer Detection and Therapy, Baldwin et al. (eds.), pp. 303-16 (Academic Press 1985), and Thorpe et al. (1982) "The Preparation and Cytotoxic Properties of Antibody-Toxin Conjugates," Immunol. Rev. 62:119-58. Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

IV. Recombinant Expression Vectors and Host Cells Used in the Methods of the Invention The methods of the invention (e.g., the screening assays described herein) include the use of vectors, preferably expression vectors, containing nucleic acid molecules encoding a POT1 protein (or a portion thereof), as well as POT1 target molecules, or portions thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., POT1 proteins, POT1 target molecules, mutant forms of POT1 proteins and/or POT1 target molecules, fusion proteins, and the like).

The recombinant expression vectors to be used in the methods of the invention can be designed for expression of POT1 proteins in prokaryotic or eukaryotic cells. For example, POT1 proteins can be expressed in bacterial cells such as *E. Coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. Coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. And Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in POT1 activity assays (e.g., direct assays or competitive assays described in detail below), or to generate antibodies specific for POT1 proteins and specific for the 12a and 15a- splice variants.

In another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. Et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to POT1 mRNA, e.g. Antisense to the 12a and/or the 15a- splice variants. Examples below describe exemplary sequences. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. Et al., Antisense RNA as a molecular tool for genetic analysis, Reviews-Trends in Genetics, Vol. 1(1) 1986.

Another aspect of the invention pertains to the use of host cells into which a POT1 or POT1 target molecule, nucleic acid molecule of the invention is introduced, e.g., a POT1 or POT1 target molecule nucleic acid molecule within a recombinant expression vector or a POT1 or POT1 target molecule nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a POT1 protein or POT1 target molecule can be expressed in bacterial cells such as *E. Coli*, insect cells, yeast or mammalian cells (such as Chinese hamster ovary cells (CHO) or COS cells). Other suitable host cells are known to those skilled in the art.

Vector DNA can be introduced-into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd. ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a POT1 protein or POT1 target molecule. Accordingly, the invention further provides methods for producing a POT1 protein or POT1 target molecule using the host cells of the invention. In one embodiment, the method comprises culturing the host cell of the invention (into which a recombinant expression vector encoding a POT1 protein or POT1 target molecule has been introduced) in a suitable medium such that a POT1 protein or POT1 target molecule is produced. In another embodiment, the method further comprises isolating a POT1 protein or POT1 target molecule from the medium or the host cell.

V. Isolated Nucleic Acid Molecules Used in the Methods of the Invention

The cDNA sequence of the isolated human POT1 gene and the predicted amino acid sequence of the human POT1 polypeptide are shown in FIGS. 3 and 6. Wild type POT1 gene sequences are disclosed, for example GEN BANK accession NM_015450, which is incorporated herein by reference in its entirety.

The methods of the invention also use isolated nucleic acid molecules that encode POT1 target molecules. The methods of the invention include the use of isolated nucleic acid molecules that encode POT1 proteins and POT1 target molecules or biologically active portions thereof, as well as nucleic acid fragments sufficient for use as hybridization probes to identify POT1-encoding and POT1 target molecule-encoding nucleic acid molecules (e.g., POT1 and POT1 target molecule mRNA) and fragments for use as PCR primers for the amplification or mutation of POT1 and POT1 target molecule nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA or may include a protein, an RNAi, an siRNA, a ribozyme, a tRNA, a mRNA, a ribosomal RNA, a snRNA, a 5SRNA, or an active portion of an RNP.

A nucleic acid molecule used in the methods of the present invention, e.g., a POT1 or POT1 target molecule nucleic acid molecule, or a portion thereof, can be isolated using standard molecular biology techniques and the sequence information provided herein. Using all or portion of the nucleic acid sequence of a POT1 or POT1 target molecule nucleic acid molecule as a hybridization probe, a POT1 or POT1 target molecule nucleic acid molecules can be isolated using standard hybridization and cloning techniques (e.g., as described in Sambrook, J. Et al., Molecular Cloning: A Laboratory Manual. 2nd. Ed., Cold Spring Harbor Laboratory, Cold Spring Harbor Laboratory Press, Cold Spring Harbor, N.Y., 1989).

Moreover, a nucleic acid molecule encompassing all or a portion of a POT1 or POT1 target molecule nucleic acid molecule can be isolated by the polymerase chain reaction (PCR) using synthetic oligonucleotide primers designed based upon the sequence of a POT1 or POT1 target molecule nucleic acid molecule.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to POT1 or POT1 target molecule nucleotide sequences can be prepared by standard synthetic techniques, e.g., using an automated DNA synthesizer.

In a preferred embodiment, the isolated nucleic acid molecules used in the methods of the invention comprise the nucleotide sequence shown in FIG. 3, 6, 7, or 9. A nucleic acid molecule which is complementary to the nucleotide sequence shown in FIG. 3, 6, 7, or 9, is one which is sufficiently complementary to the nucleotide sequence shown in FIGS. 3, 6, 7, or such that it can hybridize to the nucleotide sequence shown in FIG. 3, 6, 7, or 9, thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence shown in any one of FIG. 3, 6, 7, or 9, or a portion of any of this nucleotide sequence.

Moreover, the nucleic acid molecules used in the methods of the invention can comprise only a portion of the nucleic acid sequence of a POT1 splice variant for example, a fragment which can be used as a probe or primer or a fragment encoding a portion of a POT1 protein, e.g., a biologically active portion of a POT1 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of FIG. 3, 6, 7, or 9 or an anti-sense sequence of FIG. 3, 6, 7, or 9, or of a naturally occurring allelic variant or mutant of FIG. 3, 6, 7, or 9. In one embodiment, a nucleic acid molecule used in the methods of the present invention comprises a nucleotide sequence which is greater than 50, 50-100, 100-200, 200-300, 300-400, 400-500, 500-600, 600-700, 700-800, 800-900, 900-1000, 1000-1100 or more nucleotides in length and hybridizes under stringent hybridization conditions to a nucleic acid molecule of FIG. 3, 6, 7, or 9 or a nucleic acid sequence represented by FIGS. 2 and 5.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further preferred, non-limiting example of stringent hybridization conditions includes hybridization at 6×SSC at 45 C, followed by one or more washes in 0.2×SSC, 0.1% SDS at 65° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(C)=2(# of A+T bases)+4(# of G+C bases). For hybrids between 18 and 49 base pairs in length, $T_m$(C)=81.5+16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH2PO4, 7% SDS at about 65° C., followed by one or more washes at 0.02M NaH2PO4, 1% SDS at 65° C., see e.g., Church and Gilbert (1984) Proc. Natl. Acad. Sci. USA 81:1991-1995 (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a POT1 protein or POT1 target molecule, such as by measuring a level of a POT1-encoding nucleic acid in a sample of cells from a subject e.g., detecting POT1 or POT1 target molecule mRNA levels or determining whether a genomic POT1 or POT1 target molecule gene has been mutated or deleted.

The methods of the invention further include the use of allelic variants of human POT1, e.g., functional and non-functional allelic variants. Functional allelic variants are naturally occurring amino acid sequence variants of the human POT1 protein that maintain a POT1 activity. Functional allelic variants will typically contain only conservative substitution of one or more amino acids, or substitution, deletion or insertion of non-critical residues in non-critical regions of the protein. Non-functional allelic variants are naturally occurring amino acid sequence variants of the human POT1 protein that do not have a POT1 activity. Non-functional allelic variants will typically contain a non-conservative substitution, deletion, or insertion or premature truncation of the amino acid sequence, or a substitution, insertion or deletion in critical residues or critical regions of the protein.

The methods of the present invention may further use orthologues of the POT1 protein. Orthologues of the POT1 protein are proteins that are isolated from other organisms and possess the same POT1 activity.

The methods of the present invention further include the use of nucleic acid molecules comprising the nucleotide sequence of POT1, or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of POT1 without altering the biological activity, whereas an "essential" amino acid residue is required for biological activity. For example, amino acid residues that are conserved among the POT1 proteins from different organisms are not likely to be amenable to alteration.

Mutations can be introduced into POT1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a POT1 protein is preferably replaced with another amino acid residue from the same side chain family. Alternatively, in another embodiment, mutations can be introduced randomly along all or part of a POT1 coding sequence, such as by saturation mutagenesis, and the resultant mutants can be screened for POT1 biological activity to identify mutants that retain activity. Following mutagenesis of POT1, the encoded protein can be expressed recombinantly and the activity of the protein can be determined using an assay described herein.

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) Biotechniques 6:958-976) or intercalating agents (see, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

VI. Isolated POT1 Proteins and POT1 Target Molecules Used in the Methods of the Invention The methods of the invention include the use of isolated POT1 proteins and POT1 target molecules, and biologically active portions thereof, as well as polypeptide fragments suitable for use as immunogens to raise anti-POT1 and anti-POT1 target molecule antibodies. In one embodiment, native POT1 and POT1 target molecule proteins can be isolated from cells or tissue sources by an appropriate purification scheme using standard protein purification techniques. In another embodiment, POT1 proteins and POT1 target molecules are produced by recombinant DNA techniques. Alternative to recombinant expression, a POT1 protein or polypeptide or POT1 target molecule can be synthesized chemically using standard peptide synthesis techniques.

As used herein, a "biologically active portion" of a POT1 protein includes a fragment of a POT1 protein having a POT1 activity. Biologically active portions of a POT1 protein include peptides comprising amino acid sequences sufficiently identical to or derived from the amino acid sequence of the POT1 protein, e.g., the amino acid sequence shown in FIG. 4 or 8 which include fewer amino acids than the full length POT1 proteins, and exhibit at least one activity of a POT1 protein. Typically, biologically active portions comprise a domain or motif with at least one activity of the POT1 protein. A biologically active portion of a POT1 protein can be a polypeptide which is, for example, 25, 50, 75, 100, 125, 150, 175, or more amino acids in length. Biologically active portions of a POT1 protein or POT1 target molecule can be used as targets for developing agents which modulate a POT1 activity.

In a preferred embodiment, the POT1 protein used in the methods of the invention has an amino acid sequence shown in FIG. 4 or 8. In other embodiments, the POT1 protein is substantially identical to FIG. 4 or 8, and retains the functional activity of the protein of FIG. 4 or 8, yet differs in amino acid sequence due to natural allelic variation or mutagenesis, as described in detail in subsection V above. Accordingly, in another embodiment, the POT1 protein used in the methods of the invention is a protein which comprises an amino acid sequence at least about 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to FIG. 4 or 8.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to an amino acid sequence of having 100 amino acid residues, at least 30, preferably at least 40, more preferably at least 50, even more preferably at least 60, and even more preferably at least 70, 80, 90 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444-453 (1970)) algorithm which has been incorporated into the GAP program in the GCG software package (available online through the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers, E. and Miller, W. (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

The methods of the invention may also use POT1 and POT1 target molecule chimeric or fusion proteins. As used herein, a POT1 "chimeric protein" or "fusion protein" comprises a POT1 polypeptide operatively linked to a non-POT1 polypeptide. A "POT1 polypeptide" refers to a polypeptide having an amino acid sequence corresponding to a POT1 molecule, whereas a "non-POT1 polypeptide" refers to a polypeptide having an amino acid sequence corresponding to a protein which is not substantially homologous to the POT1 protein, e.g., a protein which is different from the POT1 protein and which is derived from the same or a different organism. Within a POT1 fusion protein the POT1 polypeptide can correspond to all or a portion of a POT1 protein. In a preferred embodiment, a POT1 fusion protein comprises at least one biologically active portion of a POT1 protein. In another preferred embodiment, a POT1 fusion protein comprises at least two biologically active portions of a POT1 protein. Within the fusion protein, the term "operatively linked" is intended to indicate that the POT1 polypeptide and the non-POT1 polypeptide are fused in-frame to each other. The non-POT1 polypeptide can be fused to the N-terminus or C-terminus of the POT1 polypeptide.

For example, in one embodiment, the fusion protein is a GST-POT1 fusion protein in which the POT1 sequences are fused to the C-terminus of the GST sequences. Such fusion proteins can facilitate the purification of recombinant POT1.

In another embodiment, this fusion protein is a protein containing a heterologous signal sequence at its N-terminus. In certain host cells (e.g., mammalian host cells), expression and/or secretion of a protein can be increased through use of a heterologous signal sequence.

Moreover, the POT1-fusion proteins used in the methods of the invention can be used as immunogens to produce anti-POT1 antibodies in a subject, to purify POT1 ligands and in screening assays to identify molecules which inhibit the interaction of POT1 with a POT1 target molecule.

Preferably, a chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). A POT1 or POT1 target molecule-encoding nucleic acid can be cloned into such an expression vector such that the fusion moiety is linked in-frame to the POT1 protein or POT1 target molecule.

The present invention also pertains to the use of variants of the POT1 proteins or POT1 target molecules which function as either POT1 agonists (mimetics) or as POT1 antagonists. Variants of the POT1 proteins or POT1 target molecules can be generated by mutagenesis, e.g., discrete point mutation or truncation of a POT1 protein or POT1 target molecule. An agonist of the POT1 proteins or POT1 target molecules can retain substantially the same, or a subset, of the biological activities of the naturally occurring form of the protein. An antagonist of a protein can inhibit one or more of the activities of the naturally occurring form of the protein by, for example, competitively modulating a POT1-mediated activity of a POT1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring forms of the POT1 protein or POT1 target molecules.

In one embodiment, variants of a POT1 protein which function as either POT1 agonists (mimetics) or as POT1 antagonists can be identified by screening combinatorial libraries of mutants, e.g., truncation mutants, of a POT1 protein for POT1 protein agonist or antagonist activity. In one embodiment, a variegated library of POT1 variants is generated by combinatorial mutagenesis at the nucleic acid level and is encoded by a variegated gene library. A variegated library of POT1 variants can be produced by, for example, enzymatically ligating a mixture of synthetic oligonucleotides into gene sequences such that a degenerate set of potential POT1 sequences is expressible as individual polypeptides, or alternatively, as a set of larger fusion proteins (e.g., for phage display) containing the set of POT1 sequences therein. There are a variety of methods which can be used to produce libraries of potential POT1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential POT1 sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acids Res. 11:477).

In addition, libraries of fragments of a POT1 protein coding sequence can be used to generate a variegated population of POT1 fragments for screening and subsequent selection of variants of a POT1 protein. In one embodiment, a library of coding sequence fragments can be generated by treating a double stranded PCR fragment of a POT1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the POT1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of POT1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify POT1 variants (Arkin and Youvan (1992) Proc. Natl. Acad. Sci. USA 89:7811-7815; Delagrave et al. (1993) Prot. Eng. 6(3):327-331).

The methods of the present invention further include the use of anti-POT1 antibodies and anti-POT1 target molecule antibodies. An isolated POT1 protein or target molecule, or a portion or fragment thereof, can be used as an immunogen to generate antibodies that bind POT1 using standard techniques for polyclonal and monoclonal antibody preparation. A full-length protein can be used or, alternatively, antigenic peptide fragments of the protein can be used as immunogens. The antigenic peptide of POT1 comprises at least 8 amino acid residues of the amino acid sequence shown in FIG. 4 or 8 and encompasses an epitope of POT1 such that an antibody raised against the peptide forms a specific immune complex with the POT1 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of POT1 that are located on the surface of the protein, e.g., hydrophilic regions, as well as regions with high antigenicity. Also preferred are epitopes of the 12a and the 15a- specific for the 12a and 15a- splice variants.

A POT1 immunogen is typically used to prepare antibodies by immunizing a suitable subject (e.g., rabbit, goat, mouse, or other mammal) with the immunogen. An appropriate immunogenic preparation can contain, for example, recombinantly expressed POT1 protein or a chemically synthesized POT1 polypeptide. The preparation can further include an adjuvant, such as Freund's complete or incomplete adjuvant, or similar immunostimulatory agent. Immunization of a suitable subject with an immunogenic POT1 preparation induces a polyclonal anti-POT1 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a POT1. Examples of immunologically active portions of immunoglobulin molecules include F(ab) and F(ab')2 fragments which can be generated by treating the antibody with an enzyme such as pepsin. The invention provides polyclonal and monoclonal antibodies that bind POT1 molecules. The term "monoclonal antibody" or "monoclonal antibody composition", as used herein, refers to a population of antibody molecules that contain only one species of an antigen binding site capable of immunoreacting with a particular epitope of POT1. A monoclonal antibody composition thus typically displays a single binding affinity for a particular POT1 protein with which it immunoreacts.

Polyclonal anti-POT1 antibodies can be prepared as described above by immunizing a suitable subject with a POT1 immunogen. The anti-POT1 antibody titer in the immunized subject can be monitored over time by standard techniques, such as with an enzyme linked immunosorbent assay (ELISA) using immobilized POT1. If desired, the antibody molecules directed against POT1 can be isolated from the mammal (e.g., from the blood) and further purified by well known techniques, such as protein A chromatography to obtain the IgG fraction. At an appropriate time after immunization, e.g., when the anti-POT1 antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. In Monoclonal Antibodies: A New Dimension in Biological Analyses, Plenum Publishing Corp., New York, N.Y. (1980); Lerner, E. A. (1981) Yale J. Biol. Med. 54:387-402; Gefter, M. L. et al. (1977) Somat. Cell Genet. 3:231-36). Briefly, an immortal cell line (typically a myeloma) is fused to lymphocytes (typically splenocytes) from a mammal immunized with a POT1 immunogen as described above, and the culture supernatants of the resulting hybridoma cells are screened to identify a hybridoma producing a monoclonal antibody that binds POT1.

Any of the many well known protocols used for fusing lymphocytes and immortalized cell lines can be applied for the purpose of generating an anti-POT1 monoclonal antibody (see, e.g., Galfre, G. et al. (1977) Nature 266:55052; Gefter, et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind POT1, e.g., using a standard ELISA assay.

Alternative to preparing monoclonal antibody-secreting hybridomas, a monoclonal anti-POT1 antibody can be identified and isolated by screening a recombinant combinatorial immunoglobulin library (e.g., an antibody phage display library) with POT1 to thereby isolate immunoglobulin library members that bind POT1. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication No. WO 92/20791; Markland et al., PCT International Publication No. WO 92/15679; Breitling et al., PCT International Publication No. WO 93/01288; McCafferty et al, PCT International Publication No. WO 92/01047; Garrard et al., PCT International Publication No. WO 92/09690; Ladner et al., PCT International Publication No. WO 90/02809; Fuchs et al. (1991) Biotechnology (NY) 9:1369-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrard et al. (1991) Biotechnology (NY) 9:1373-1377; Hoogenboom et al. (1991) Nucleic Acids Res. 19:4133-4137; Barbas et al. (1991) Proc. Natl. Acad. Sci. USA 88:7978-7982; and McCafferty et al. (1990) Nature 348:552-554.

Additionally, recombinant anti-POT1 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al., International Application No. PCT/US86/02269; Akira et al., European Patent Application No. 184,187; Taniguchi, M., European Patent Application No. 171,496; Morrison et al., European Patent Application No. 173,494; Neuberger et al., PCT International Publication No. WO 86/01533; Cabilly et al., U.S. Pat. No. 4,816,567; Cabilly et al., European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559; Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyen et al (1988) Science 239:1534; and Beidler et al. (1988) J. Immunol. 141:4053-4060.

An anti-POT1 antibody can be used to detect POT1 protein (e.g., in a cellular lysate or cell supernatant) in order to evaluate the abundance and pattern of expression of the POT1 protein. Anti-POT1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

EXAMPLES

The following non-limiting examples are illustrative of the invention.

Example 1

POT1 Alternative Splicing Variants in Human Cell Lines

Exons 12 to 16 of POT1 cDNA were amplified to detect the presence of difference splice forms. Two additional bands were present in mismatch-repair deficient cells, but not in proficient human cell lines. The additional bands were sequenced and shown to be splice variants of POT1. In lanes HCT116, HCT15, and HEC59 the upper band was splice variant 12a (variant 2) and the medium band was splice variant 15a-, which lacks the last 18 nucleotides of splice variant 15a (variant 5). See FIG. 1. The sequence of Exons 15a and 15a- are shown in FIG. 9.

Example 2

Protocol for Determining POT1 Variant Biomarkers

Prepare RNA from tissues, culture cells or blood samples with the RNeasy Mini Kit from QIAGEN, following the manufacturer's directions.

cDNA Preparation:

A. Treat isolated RNA with Amp DNase I (Invitrogen)

1). Reaction:

2 μg total RNA (from step 1)

1 μl 10× buffer

1 μl Dnase I, 1 U/μl

Amp Water to 10 μl

2). Incubation 15', RT

3). Add 1 μl 25 mM EDTA, heat for 10', 65° C., then on ice 2'.

B. ABI kit (N808-0234, TaqMan Reverse Transcription Reagents) to make cDNA

| | |
|---|---|
| 10× Buffer | 5 μl |
| 25 mM MgCl2 | 11 μl |
| dNTPs | 10 μl |
| Random Hexamers | 2.5 μl |
| Rnase Inhibitor | 1 μl |
| MultiScript | 1.25 μl |
| RNA sample (step 1) | 11 μl |
| Amp Water to | 50 μl |

Program: 25° C. for 10', 48° C. for 30', 95° C. for 5'

PCR Amplification:

1) Make 20 μl of the PCR components with 2 μl of cDNA template (from step 2), following the manufacturer's directions.

2). Denature the template for 5 min at 94° C. Perform 30-40 cycles of PCR amplification as follows:

Denature: 94° C. for 30 s

Anneal: 55° C. for 30 s

Extend: 72° C. for 1 min

Analyze the products by 1.2% agarose gel electrophoresis.

Example 3

Real-time PCR of POT1(ABI 7700)

POT1 alternative splicing variants in human cell lines were amplified by Real-time PCR by the following protocol:

1) 20 μl of the PCR components were made with 2 μl of cDNA template (from step 2), following the manufacturer's directions (SYBR Green PCR master mix, ABI).

2) Step 1) above, was performed for 2 min at 50° C. and step 2 for 10 min for 95° C. Perform 40 cycles of PCR amplification for 15 s at 95° C. and 1 min at 60° C. The products were analyzed by ABI real-time PCR software and results were then graphed.

The POT1 variant 12a was amplified with primers 12a/12aB:

```
Pot1-12A:  5' TTC AGA TGT TAT CTG TCA ATC AGA ACC
           TG
           (SEQ ID NO: 8)

POT1-12aB: 5' GGA GGT GGA GGC TGC AAT GAG
           (SEQ ID NO: 9)
```

The POT1 variant 15a- was amplified with primers 15A/15aB2:

```
POT1-15A:    5' ATG TCT ACT TTT GAT AGA AG
             (SEQ ID NO: 10)

POT1-15aB2:  5' TGA GTG TAC CTC CTT GAG TA
             (SEQ ID NO: 11)
```

Figure 11:
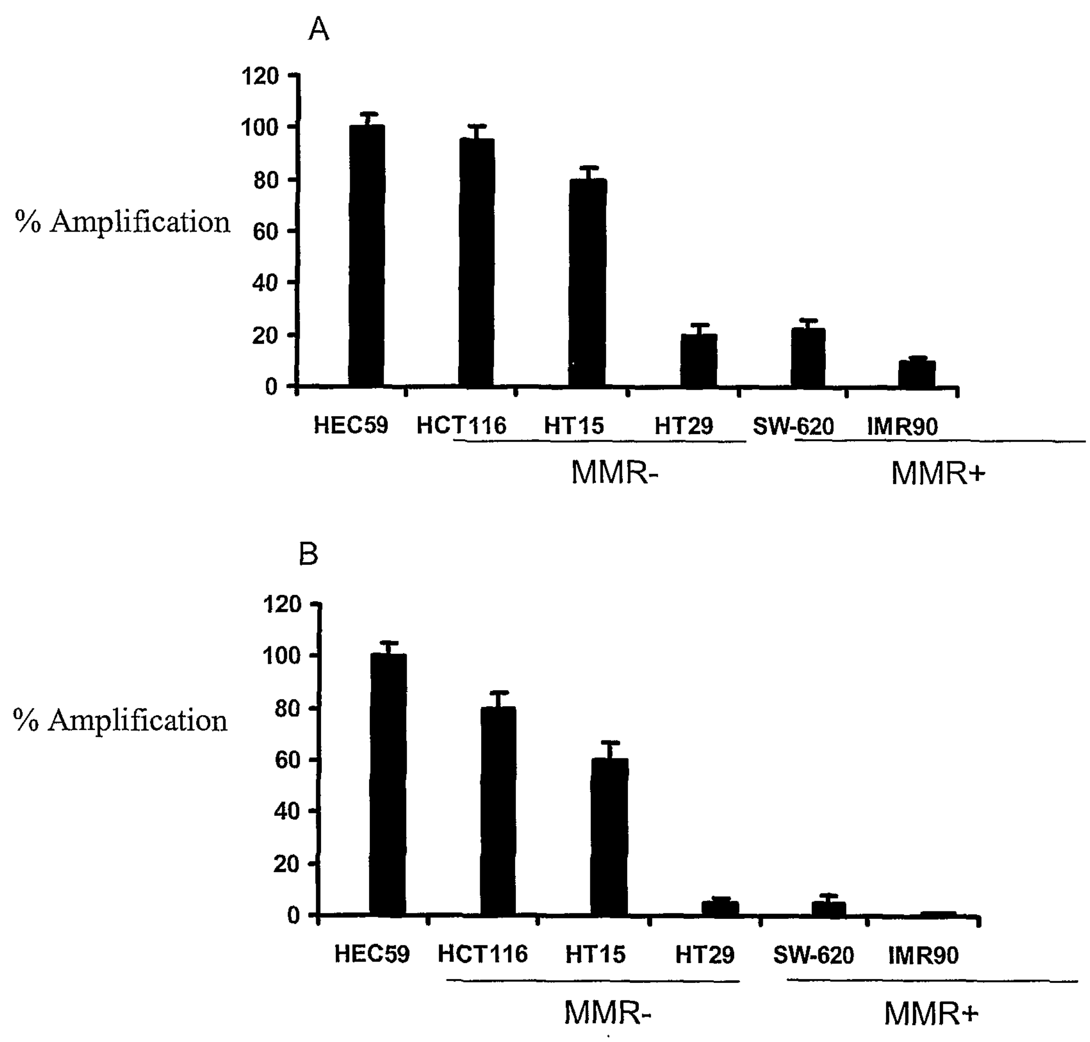
FIG. 11 depicts POT1 alternative splicing variants in human cell lines that were amplified by Real-Time PCR.

FIG. 11A shows that the MMR− cells, HEC59, HCT116, and HT15 were positive for the 12a variant, while the MMR+ cells, HT29, SW-620, and IMR90 were not.

FIG. 11B shows that the MMR− cells, HEC59, HCT116, and HT15 were positive for the 12a variant, while the MMR+ cells, HT29, SW-620, and IMR90 were not.

Example 4

Sequences of POT1 PCR Primers

PCR Primers for Amplifying the Wild-type POT1, 12a and 15a- Variants:

```
Pot1-12A:  5' TTC AGA TGT TAT CTG TCA ATC AGA ACC
           TG
           (SEQ ID NO: 8)

Pot1-16B:  5' ATG TAT TGT TCC TTG TAT AAG AAA TGG
           TGC
           (SEQ ID NO: 12)
```

PCR Primers for Amplifying the Wild-type POT1 and 12a Variants:

```
Pot1-11A:    5' TAG CCT TCA TAC CAA ACT TCA ATC
             (SEQ ID NO: 13)

Pot1-15B1:   5' TTA TAT CCA AAT CGC CCT CAT
             (SEQ ID NO: 14)
```

PCR Primers for Amplifying the 12a Variant:

```
Pot1-9A:   5' GGG CAA AGC AGA AGT GGA CGG AGC ATC
           (SEQ ID NO: 15)

POT1-12aB: 5' GGA GGT GGA GGC TGC AAT GAG
           (SEQ ID NO: 9)
```

PCR Primers for Amplifying the 15a Variant:

```
Pot1-13A:    5' ACG AGG TAG AAA GAT GTC AA
             (SEQ ID NO: 16)

POT1-15aB:   5' TGA GTG TAC CTC CTT GAG TA
             (SEQ ID NO: 17)
```

PCR Primers for Amplification the 15a- Variant:

```
POT1-15A:    5' ATG TCT ACT TTT GAT AGA AG
             (SEQ ID NO: 10)

POT1-15aB2:  5' TGA GTG TAC CTC CTT GAG TA
             (SEQ ID NO: 11)
```

Example 4

Generation of an Anti-POT1-12a Splice Variant Antibody

Peptide Sequence of Anti-POT1-12a Splice Variant Antibody

```
NGVSLRPPGWSSVARSRLIAASTS
(SEQ ID NO: 18)
```

Method:

POT1 peptide was synthesized, conjugated to KLH, and used to immunize rabbits.

Example 5

Sequences of siRNA for POT1 Splice Variants

```
siRNA-POT1-12a
CCTGAGTTCAAGCTTCTCC
(SEQ ID NO: 19)

siRNA-POT1-15a-
AAGTACTCAAGGAGGTACA
(SEQ ID NO: 20)
```

TABLE I

POT1 12a/15a-splicing variants in cell lines*

| MMR | Cell line | Number | Positive of POT1-12a/15a- | Total |
|---|---|---|---|---|
| MMR− | Colon cancer | 6 | 6/6 | 8 |
| | Non-colon cancer | 2 | 2/2 | |
| MMR+ | Colon cancer | 3 | 0/3 | 7 |
| | Normal | 4 | 0/4 | |
| MMR-ND** | Others | 11 | 0/11 | 11 |

*Determined by PCR with primers 12A/16B.
**ND: not determine.

TABLE II

POT1 12a/15a-splicing forms in primary tissue*

| MMR | Sample | Number | Positive of POT1-12a/15a- |
|---|---|---|---|
| HNPCC | Colon or Rectum cancer | 8 | 8/8 |
| MSI | Colon or Rectum cancer | 11 | 11/11 |
| MSS | Colon or Rectum cancer | 21 | 1/21 |
| MMR− | Normal tissue | 8 | 0/8 |
| MMR-ND** | Lung cancer | 10 | 0/10 |

*Determined by PCR with primers 12A/16B.
**ND: not determine

Tables 1 and 2 summarize results from PCR reactions in cell lines and primary tissues. The tables demonstrate that the correlation of POT1 variants and MMR tumor tissues.

The disclosures of each and every patent, patent application and publication cited herein are hereby incorporated herein by reference in their entirety.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. A method of treating a digestive tract tumor comprising administering to a subject in need thereof an effective amount of:

i) an antisense RNA of Protection of Telomeres Protein 1 (POT1) splice variant 12a, ii) an antisense RNA that has at least 85% sequence identity to POT1 splice variant 15a-, or iii) an RNA that specifically binds and inactivates a POT1 15a, POT1 15a-, or POT1 12a splice variant.

2. The method of claim 1, wherein the digestive tract tumor is a colorectal carcinoma.

3. The method of claim 1, wherein the digestive tract tumor is hereditary nonpolyposis colorectal carcinoma (HNPCC).

4. The method of claim 1, wherein the RNA that specifically binds and inactivates a POT1 15a, POT1 15a-, or POT1 12a splice variant is an RNAi, siRNA, antisense RNA, or ribozyme.

* * * * *